United States Patent [19]

Orr, Jr.

[11] Patent Number: 4,565,086
[45] Date of Patent: Jan. 21, 1986

[54] METHOD AND APPARATUS FOR DETECTING ENTRAINED GASES IN FLUIDS

[75] Inventor: Raymond T. Orr, Jr., Norman, Okla.

[73] Assignee: Baker Drilling Equipment Company, Orange, Calif.

[21] Appl. No.: 572,436

[22] Filed: Jan. 20, 1984

[51] Int. Cl.⁴ .............................................. G01N 25/20
[52] U.S. Cl. .......................................... 73/23; 175/40; 175/66; 436/30
[58] Field of Search ........................... 73/29, 23, 27 R; 422/94, 96, 98; 436/29, 30; 175/40, 50, 66

[56] References Cited

U.S. PATENT DOCUMENTS

| | | | |
|---|---|---|---|
| 3,421,362 | 1/1969 | Schaeffer | 422/94 |
| 3,447,359 | 6/1969 | Kapff | 73/23 |
| 3,520,657 | 7/1970 | Frumerman | 73/23 |
| 3,537,296 | 11/1970 | Gamache | 73/23 |
| 3,581,473 | 6/1971 | Ririe, Jr. et al. | 73/23 |
| 3,607,084 | 9/1971 | Mackey et al. | 73/27 R |
| 3,888,109 | 6/1975 | Sharki et al. | 73/23 |
| 3,957,947 | 8/1976 | Kruishood | 73/16 |
| 4,250,142 | 2/1981 | Kollmai | 422/94 |
| 4,305,724 | 12/1981 | Micko | 436/156 |
| 4,341,108 | 7/1982 | Warncke et al. | 73/23 |
| 4,351,614 | 9/1982 | Garnier | 73/16 |
| 4,384,925 | 5/1983 | Stetter et al. | 73/16 |
| 4,385,910 | 5/1983 | Eilers et al. | 73/16 |

*Primary Examiner*—David L. Lacey
*Attorney, Agent, or Firm*—Norvell & Associates

[57] ABSTRACT

Apparatus and method for detecting the level of gases entrained within a circulating drilling fluid used in subterranean well operations are disclosed. Detection of incipient gas kicks during drilling operations is accomplished by detecting the level of entrained gases. A gas-air sample is gathered at the surface of the well, and a gas-air sample having a constant relative humidity is delivered at a constant volumetric flow rate to gas sensors. Dilution air is automatically added to the sample when the gas concentration exceeds a known limit. Automatic periodic calibration of the sensors is provided. Stable signals from the gas sensor are obtained at two distinct flow rates.

23 Claims, 13 Drawing Figures

METHOD AND APPARATUS FOR DETECTING ENTRAINED GASES IN FLUIDS

BACKGROUND OF THE INVENTION

1. Field of the Invention:

This invention relates to the detection of gases produced in subterranean oil and gas wells during drilling operations and the monitoring of gas levels to detect incipient gas kicks.

2. Description of the Prior Art:

In conventional drilling operations, a drilling fluid or drilling mud is continuously circulated between the drill bit and the surface of the well. Minute quantities of gas may be entrained in this circulating drilling fluid and delivered to the surface where they can be identified by a gas detector. In conventional gas detection systems, a motor driven vaccum pump draws air through a gas trap mounted in the drilling fluid flow line and the trapped gas is transported to an on-site laboratory. The gas is then passed through a filter, a flow meter and a hot wire bridge type gas detector having two filaments maintained at different temperatures to make it possible to distinguish between wet and dry gas. Conventional instruments which are manually operated, can detect as little as 0.01 cubic feet of gas per hour mixed with the air drawn from the trap. The gas detector can be connected to a recording apparatus so that the signal appears on the recorder chart. Absolute values of gas concentrations cannot be obtained in this manner since the amount of air mixed with the fluctuating levels of gas in the circulating fluid does not remain constant. Relative changes in the level in the drilling fluids can, however, be detected by an operator. With these conventional systems, the operator must also continuously compensate for changes in sensitivities of the sensors and must adjust his gas detector system based upon the relative levels of gas detected. For example, some conventional sensor units have an upper limit on the gas concentration at which they can be employed while other sensor elements can only detect relatively high gas concentrations. It is therefore conventional practice for gas detection systems to employ multiple sensors for use in different flow ranges. The operator must therefore determine which sensor is to be employed to give an accurate detection of gas levels. Since absolute gas concentrations cannot be obtained with conventional systems, the operator's choice of sensor levels is subject to interpretation and to error.

Another prior art method of employing conventional manual sensor systems is to use a single sensor capable of detecting relatively low gas concentrations and to dilute the gas sample with ambient air to reduce the absolute level of the sensor signal. Corresponding range changes to compensate for variable manual dilution must also be made in order to monitor the gas levels present. Such changes make it difficult to determine the exact levels of hydrocarbon gases present in the circulating drilling fluid, and the driller will therefore be unsure if he has encountered a gas pocket and if a gas kick is imminent. These random changes in signal level can also make a permanent record of gas level difficult to interpret.

SUMMARY OF THE INVENTION

Apparatus and method for use in detecting the presence of combustible gases produced from a subterranean formation and entrained in a fluid circulated through the subterranean well includes gas gathering apparatus, a gas-air sample pump subassembly and a local control subassembly. Combustible gases are liberated from the circulating fluid by a gas trap. Fluids and solids are removed from the gas-air sample. The pressure of the gas-air sample is increased by a pump with the relative humidity equal to 100%. When the pressure is subsequently lowered, a constant relative humidty of the gas-air sample to be delivered to the sensors can be established. The gas-air sample is transported to a combustible gas diffusion sensor at a constant flow rate. The gas-air sample moves horizontally past a vertically mounted sensor. The sensor mounting permits vertical diffusion of gases from the gas-air sample, and, within the flow limits established by a sample flow controller, the output signal from the sensor for a known gas concentration remains constant. The upper limit of combustible gases with which the sensor can operate is less than the gas concentrations which can occur. Dilution air can be injected into the gas-air sample upstream of the sensor to reduce the concentration of gas presented to the sensor. The volumetric flow rate with dilution air exceeds the volumetric flow rate without dilution air. The output of the combustible gas sensor varies with flow rate. A chamber is provided such that the output of the sensor with dilution air does, however, remain constant within the variations in flow rate which would occur during normal operation of the sample flow controller. The output of the sensor with dilution air is, however, significantly different from the output without dilution air. A controlling microprocessor corrects the output such that an accurate signal is provided for situations with or without dilution air.

DETAILED DESCRIPTION OF THE PREFERRED EMBODIMENT

Figure 1:
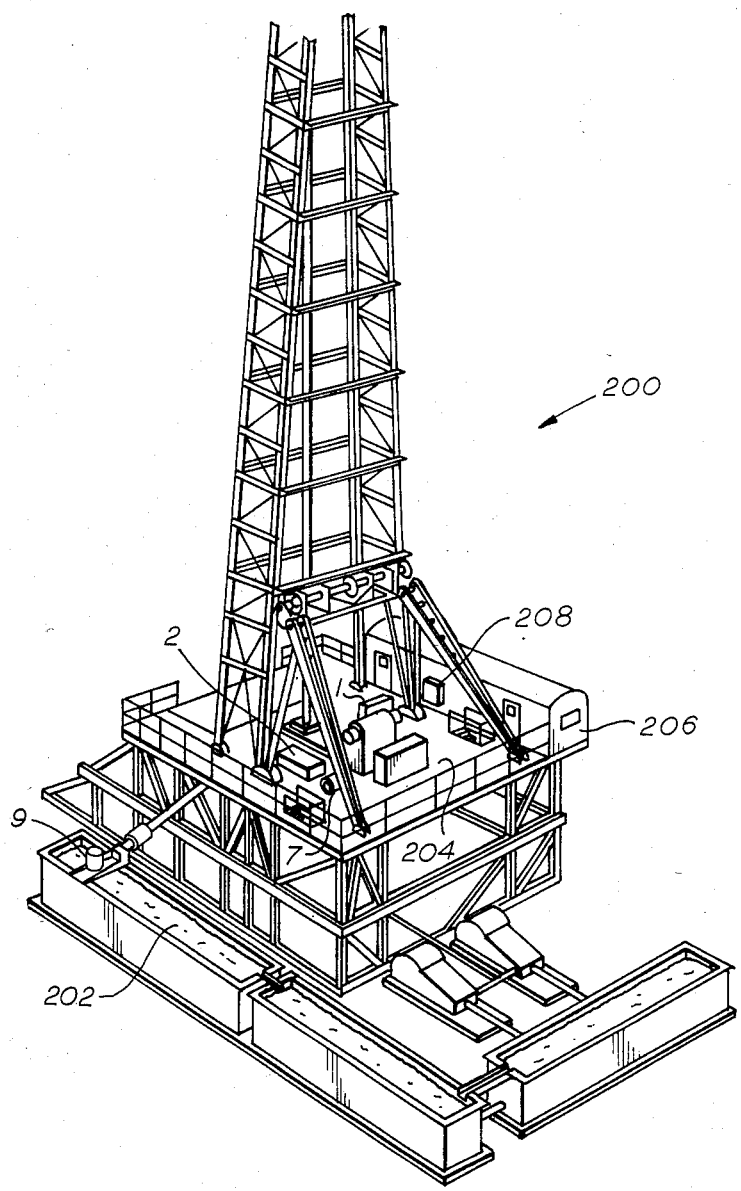
FIG. 1 depicts a conventional drilling rig with which the gas detector can be utilized.

FIG. 1 depicts a conventional drilling rig 200 with which the gas detector comprising the preferred embodiment of this invention can be used. FIG. 1 shows the gas detector remote display box 1, the local control box 2 and the sample air pump assembly 7 located on the drilling floor 204. The gas trap 9 is located at the shale shaker 202 in the vicinity of tanks holding drilling mud circulated upwardly from the well bore. The gas detection remote display unit 1 is shown on the rig floor and can be used by the driller. An alternate display unit 208 can be located in trailer 206 or at some other position in the vicinity of the rig or elsewhere.

As a subterranean well bore for an oil or gas well is drilled, a fluid is continuously circulated through the well bore from the surface to the vicinity of the drill bit and returning to the surface. This fluid is commonly referred to as drilling mud. Drilling mud is a mixture of clay, water and chemical additive pumped downhole through the drill pipe and drill bit. The mud cools the rotating bit; lubricates the drill pipe as it rotates; carries cuttings to the surface; and serves to prevent the wall of the bore hole from crumbling or collapsing. Drilling mud also provides a hydrostatic head to prevent extraneous fluids, including gases present in subterranean formations, from entering the well bore or from rapidly exiting the well bore. In this manner downhole pressures can be controlled during drilling. Fluids produced in subterranean formations will, however, inevitably become entrained in the drilling mud and will be circulated to the surface. FIG. 1 shows the shale shaker 202 where cuttings are sifted from the drilling mud. At the shale shaker, the drilling mud is accessible so that gases entrained in the drilling mud can be gathered by gas trap 9. In a conventional drilling rig assembly the shale shaker 202 is the first location in which the drilling mud is accessible after it is returned from the subsurface drill bit location through the well bore to the surface.

Figure 2:
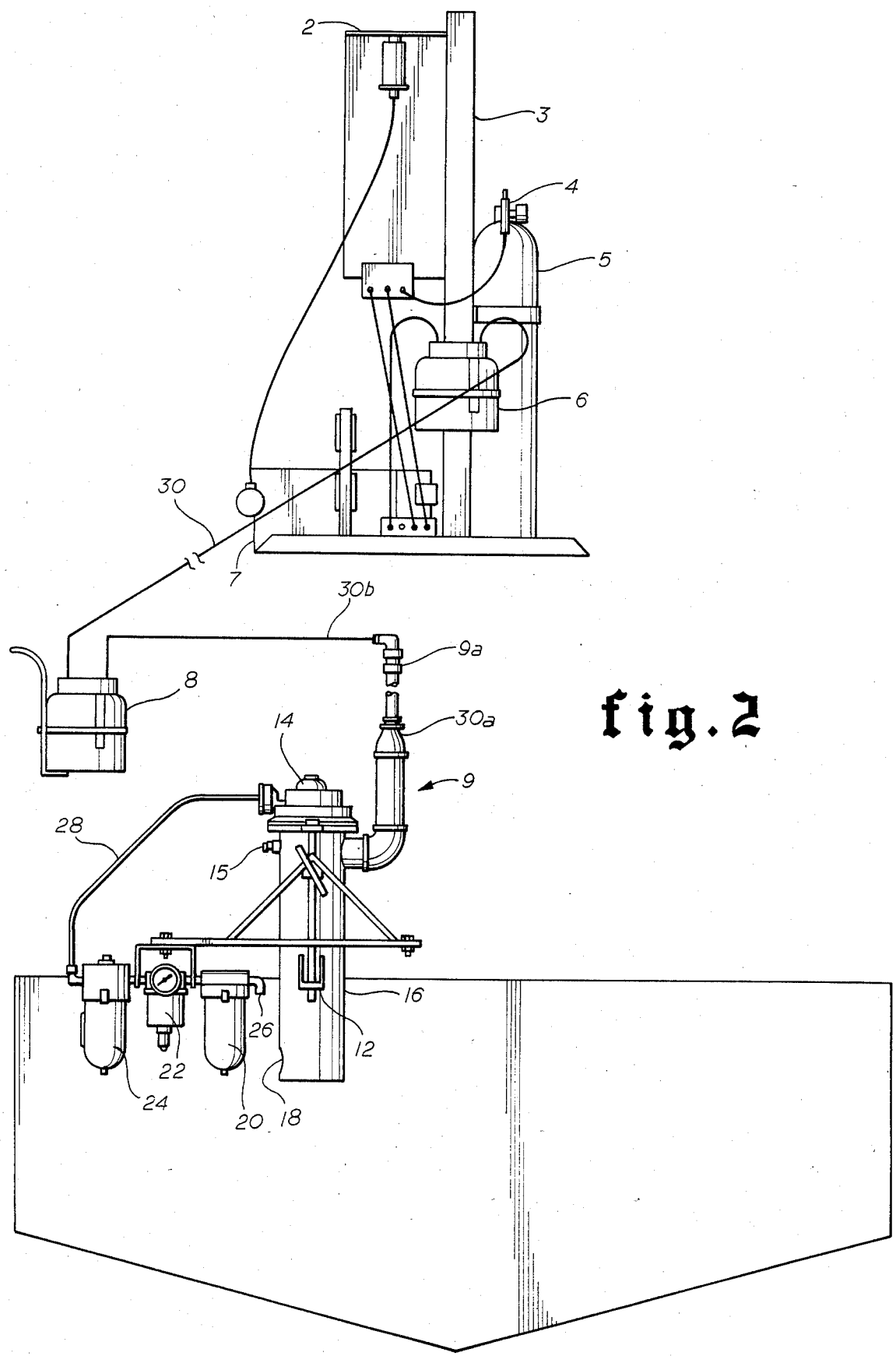
FIG. 2 depicts the interconnected gas gathering subassembly, the air/sample pump subassembly and the control subassembly of the gas detector.

Inasmuch as combustible liquids and gases can be mixed with the drilling mud, the vicinity of the shale shaker is normally considered a hazardous area in that fumes are often present this vicinity. In FIG. 2, a conduit or sample flow line 30 is shown extending from the gas gathering trap 9 to an air sample pump assembly 7 which can be spaced from the hazardous area at the shale shaker. Gases gathered by the gas trap are transported through flow line 30 to the air sample pump and are subsequently transported to a control subassembly 2. Sensors for detecting the relative level of combustible gas present in the sample gathered from the drilling mud, are located in the control subassembly 2. Signals from the sensor and associated hardware at the local control subassembly 2 are then transmitted to output units 1 and 208 which may be located in less hazardous areas.

FIG. 2 shows the components of the gas gathering subassembly and the elements of the air sample pump and flow control subassemblies. The gas trap 9 is positioned at the shale shaker with the lower portion of the gas trap housing 16 extending below the mud level so that port 18 extending into the interior of the mud housing is located in the drilling mud. In the preferred embodiment of this invention, the housing 16 is sufficiently long so that the gas trap subassembly 9 can be used for varying mud levels which can be anticipated during drilling operations. An agitator 12 located within the gas trap housing and driven by an air motor 14 is also positioned to extend into the circulating drilling mud. The agitator 12 disturbs the circulating liquid and liberates gases entrained within the circulation drilling mud. The air motor 14 is driven by the rig air supply communicating through conduit 26. An air filter 20, an air pressure regulator 22, and an air lubricator 24 prepare the rig air for driving the conventional air motor 14. Entrained gases liberated by agitator 12 are intermixed with ambient air introduced into gas trap housing through an inlet 15. The liberated produced gases and the ambient air mixture then travel into sample flow line 30, initially through a vertically extending section 30a.

The produced gases liberated from the drilling mud at gas trap 9 will normally be combustible hydrocarbons released from subterranean formations penetrated by the well bore. Therefore electrical apparatus which might tend to ignite these combustible gases are not positioned in the vicinity of the gas gathering subassembly because of the presence of hazardous gases. Furthermore, the temperature of the drilling mud at the shale shaker will generally be greater than the temperature of the ambient air at the well surface. Combustible gases entrained within the hotter drilling mud will also have a temperature greater than the ambient air. Vertical section 30a of sample flow line 30 will provide a means for transporting the gas-air sample mixture away from gas trap 9 and away from the elevated temperatures at the surface of the mud tanks.

It can be expected that the sample gas-air mixture gathered by gas trap 9 will contain a large amount of water vapor. Vertical section 9a will permit at least a portion of this water vapor to condense. At least a portion of the liquids and solids which may be entrained within the gas-air sample would also tend to gravitate out as the air-gas sample moves through vertical section 30a. The velocity of the gas-air sample in vertical section 30a will be insufficient to transport much of the entrained solids and liquids to the downstream portions of the sample flow line 30.

Air sample flow section 30b extends from vertical section 30a to a glycol reservoir 8 though which the gas-air sample is bubbled. The glycol reservoir serves to remove moisture and other liquids or solids which may remain in the gas-air mixture. The gas-air sample is then transferred from the glycol reservoir through the next downstream section of sample flow line 30 to a condensation reservoir located in the vicinity of the air sample subassembly and the local control subassembly. In the preferred embodiment of this invention, the condensate trap 6 is positioned on a mounting stand 3. Local control box 2 is also located on mounting stand 3 immediately above the sample/air pump subassembly 7. A source of calibration gas 5 and a calibration gas pressure regulator 4 are also positioned adjacent local control box 2 with a suitable connecting line extending from the calibration gas regulator to local control box 2.

Figure 3:
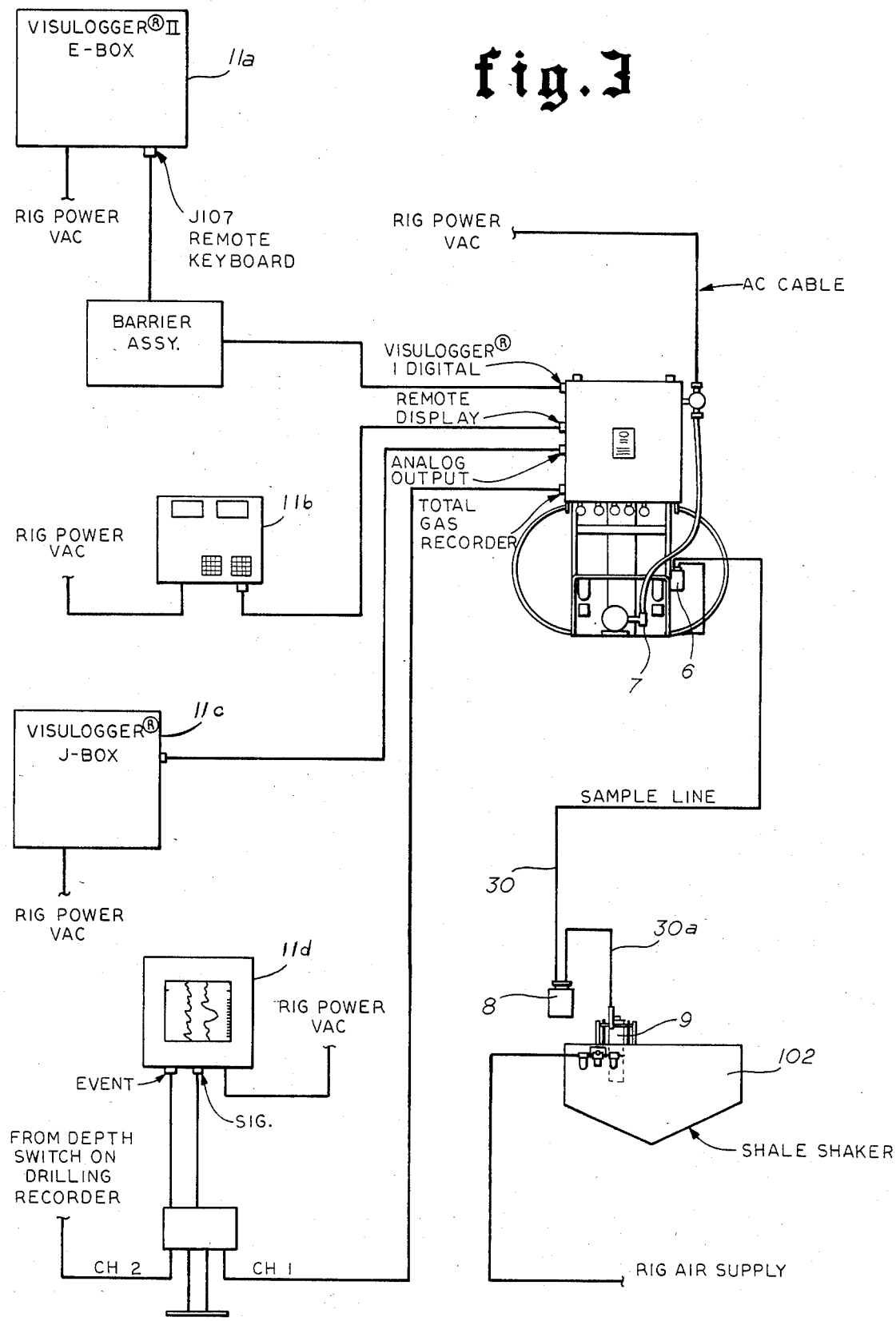
FIG. 3 is a schematic illustrating the interconnections between the gas detector subassemblies and output apparatus.

FIG. 3 shows the interconnection of the gas detection system with one or more remote display devices. Digital or analog outputs can be supplied through the local control subassembly to a plurality of output displays 11a–11d. For example, signals may be displayed on a Visulogger I or Visulogger II system. Visulogger is a registered trademark of Totco, Inc., a subsidiary of Baker International Corporation. The Visulogger systems comprise microprocessor based remote display systems in which drilling parameters or tripping parameters can be displayed at a remote location. For example, pertinent drilling parameters can be displayed to the driller during drilling operations. Each of the Visulogger systems employs an enclosed safety barrier assembly or junction box having passive devices limiting the voltage and current received or transmitted from the local control subassembly 2. A measurement of gas detected in the circulated drilling fluid can be output on the Visulogger systems together with other pertinent drilling parameters. In the alternative, a separate remote display 11b in which only the gas detection measurement as output can also be employed. A total gas record can also be displayed in strip chart form by a strip chart recorder 11d.

Figure 4:
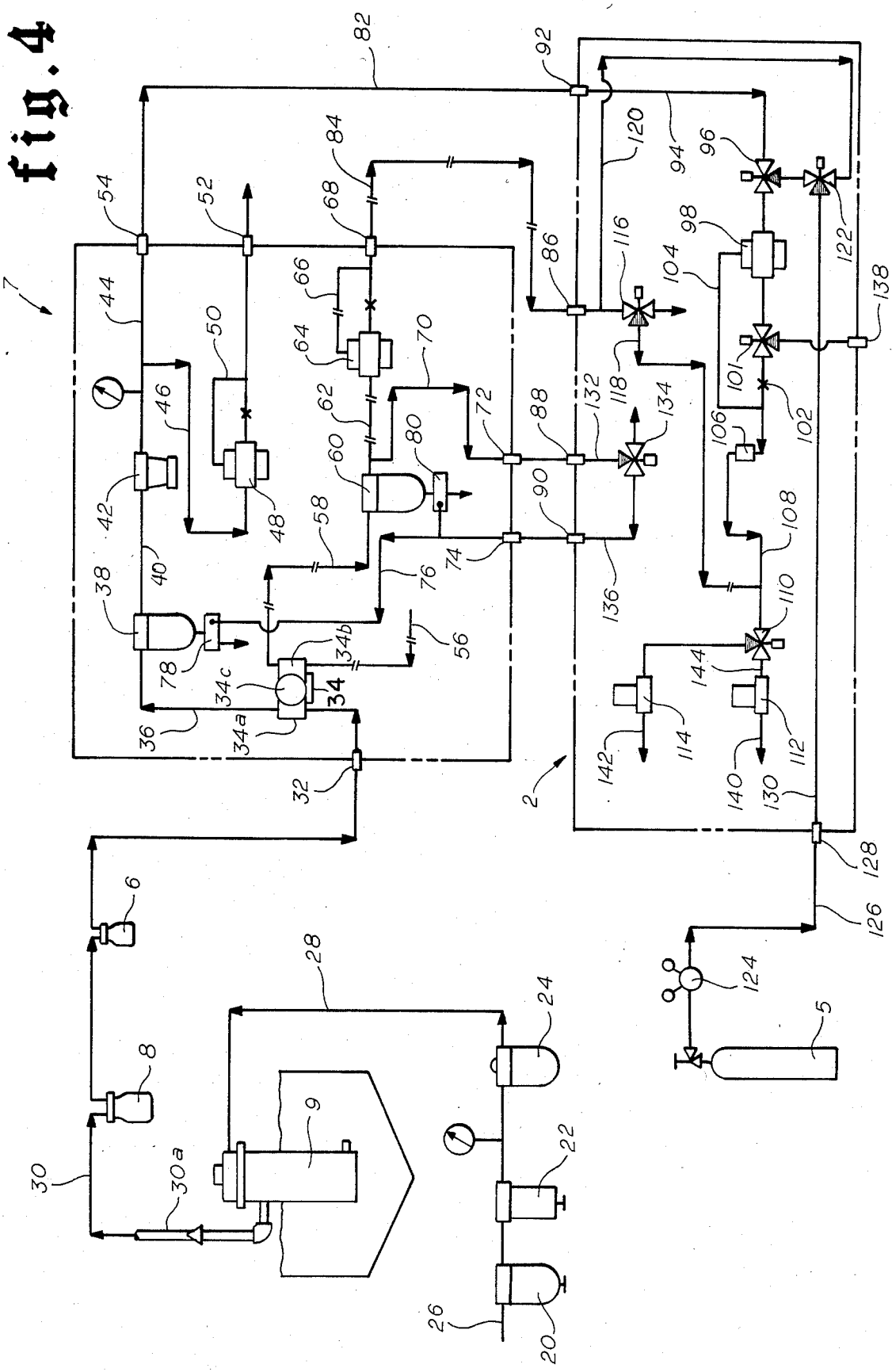
FIG. 4 is a flow schematic of the gas detector system.

The collection, transportation, preparation and sensing of a combustible gas entrained in circulating drilling fluid is illustrated in schematic fashion in FIGS. 4-8. FIG. 4 shows the gas gathering subassembly including gas trap 9, the air sample pump subassembly 7, and the local control subassembly 2, and depicts the flow of the gas-air sample from the shale shaker to the gas sensors 112 and 114. As described in more detail with reference to FIG. 2, a gas-air mixture is collected by gas trap 9 and is transmitted through sample flow line 30 to a glycol reservoir 8 and a condensation trap 6. During transportation of this sample through flow line 30, the gas-air sample is cooled, initially in the vertically extending section 30a of the sample flow line. After the gas-air sample passes through the glycol reservoir 8 and the condensation trap 6, a significant amount of moisture and other contaminates, such as solid particles entrained in the fluid flow, have been removed. The gas-air sample is then transported through sample inlet 32 to the air sample pump 7.

The pressure of the gas-air mixture in the flow line 30 at sample inlet 32 will normally be less than ambient. A diaphragm pump 34 having two diaphragms 34a and 34b operated by a single motor 34c is located adjacent the sample inlet 32. The gas-air sample in flow line 30 is introduced on only one side of the two diaphragm pump 34. After passing through pump stage 34a, the pressure of the gas-air mixture in flow line 36 has been increased above ambient pressure. The gas-air mixture in flow line 36 will, in general, be saturated or nearly saturated with water vapor and may contain excess water droplets thus, the air-gas mixture will have a relative humidity of 100% or nearly 100%. A sample coalescing filter 38 is located along flow line section 36 and excess moisture will be removed during passage through the coalescing filter. Immediately downstream of coalescing filter 38 in flow line 40, the gas-air mixture will be essentially saturated. A sample pressure regulator 42 is located downstream of filter 38, and regulator 42 reduces the pressure of the gas-air sample to approximately 15 psi. Since the amount of water vapor in the gas-air sample remains constant as the sample moves through pressure regulator 42, the relative humidity of the gas-air sample is reduced to a value less than 100%, because the partial pressure of the water vapor in the gas-air mixture in flow line 40 is less than the saturation pressure in flow line 44 resulting in a reduction in the relative humidity after the pressure of the system is lowered by the sample pressure regulator 42. The quantity of water vapor in the gas-air mixture in the sample flow line will remain constant through the gas detection system downstream of sample pressure regulator 42. Thus the relative humidity of the gas-air mixture exposed to sensors 112 and 114 will be constant at a value less than 100%.

A bypass flow line 46 intersects sample flow line 44 downstream of the sample regulator 42. A conventional bypass flow regulator 48 located on bypass flow line 46 maintains a constant differential pressure on opposite sides of an orifice located downstream of the bypass flow controller. A constant flow rate of gas-air mixture is thus maintained through the orifice. Bypass flow passage 46 is connected to a vent 52 downstream of the bypass flow controller 48. A portion of the gas-air sample in flow line 44 can thus be removed through bypass flow passage 46 at a constant rate. The remaining portion of the gas-air mixture in flow line 44 can then be transported through a sample outlet 54 into a sample flow tube 82. The reduced volume of gas-air mixture exiting the air sample pump assembly can be more rapidly transported to the sensors so that fluctuations in the concentration of gas in the gas-air mixture can be detected more rapidly by sensors 112 and 114. More importantly, bypass flow controller 48 insures that air will be drawn into the system at the gas gathering subassembly in addition to the entrained gases liberated from the drilling mud. Therefore the gas-air samle initially delivered to the system will have a reduced gas concentration. Saturation of the system when large amounts of gas entrained in the drilling mud, which would occur during a kick, can be delayed, and appropriate relative levels of gas concentration can be detected.

The gas-air sample is transported from the air sample pump assembly 7 to the local control assembly 2 by means of external flow line 82. Flow line 82 communicates with a sample inlet 92 to introduce the gas-air mixture into flow line 94 within the local control assembly. A conventional solenoid valve 94 is located along flow line 94. In the configuration of FIG. 4, the solenoid valve is shown with two aligned ports open to permit flow therethrough. A third port, the cross hatched port, is shown in the closed position in FIG. 4. In each of the flow diagrams discussed herein, the hatched outlet of a conventional solenoid valve is closed. The gas-air mixture in flow line 94 is transported through solenoid valve 96 to sample flow controller 98. Sample flow controller 98 is a conventional apparatus adapted to maintain a constant differential pressure across a downstream orifice, here repesented schematically at 102. Again, a constant differential pressure across orifice 102 results in a constant volumetric flow rate through orifice 102 and in the flow line 108 downstream. It will of course be understood that conventional mass flow controllers can be substituted for the volumetric flow controllers used herein. After passing through orifice 102, the gas-air mixture passes through a flow switch 106 capable of determining if the gas-air mixture is flowing therethrough. If no gas-air mixture is flowing through flow switch 106, the flow switch will transmit a signal indicating that any readings from sensors 112 and 114 should be ignored. In the configuration of FIG. 4, the gas-air mixture in flow line 108 subsequently passes through a conventional solenoid valve 110 permitting flow into sensor inlet 144. The gas-air mixture is thus introduced to a sensor 112 at a constant volumetric flow rate and at a constant relative humidity less than 100%. Sensor assembly 112 comprises a sensor capable of detecting the relative amount of gas in the gas-air mixture and of transmitting a corresponding signal. In the preferred embodiment of this invention, the sensor 112 comprises a sensor, generically referred to as a hot wire sensor which can include a catalytic bead sensor, capable of detecting the presence of combustible gases. A vent 140 is located downstream of sensor 112, and any remaining gas-air mixture and any combustion by-products generated by operation of the sensor are vented to the atmosphere.

Figure 5:
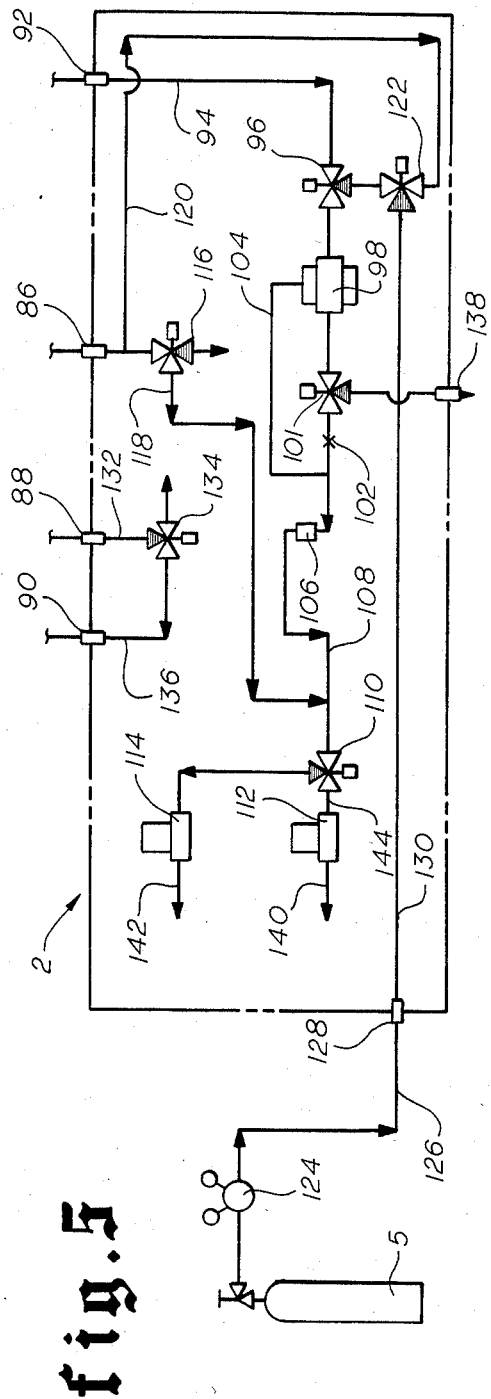
FIG. 5 is a flow schematic of the flow control subassembly showing the sample dilution flow regime.

Conventional combustible gas detecting sensors have an upper limit on the detectable concentration of gas. For example, a conventional hot wire type or catalytic bead type sensor capable of detecting combustible gases may have an upper limit equal to a 5% gas concentration in the gas-air mixture. This relatively low limit on the gas concentration detectable by conventional sensors is incompatible with the gas concentrations which could be expected to occur when a significant amount of gases produced from a subterranean formation are entrained in the circulating fluid liberated at gas trap 9. An air dilution path is provided in the air sample pump subassembly 7 and the local control subassembly 2 to further dilute the gas-air sample when the original concentration of gas in the sample exceeds predetermined value. When sensor 112 detects a gas concentration equal to the predetermined upper limit, suitable control means are actuated to open the air dilution flow path to communicate with the air sample flow line 108 upstream of sensor 112. This air dilution flow stream is shown in FIGS. 4 and 5. FIG. 4 shows the air dilution flow line in its closed position. Ambient air is collected through an intake 56 and is pumped through diaphragm stage 34b operated by pump motor 34c. The ambient air in flow line 58 downstream of the pump assembly passes through an air coalescing filter 60 to remove contaminates and to remove condensed water vapor. Air then flows from air coalescing filter 60 to an air flow controller 64, similar to flow controllers 48 and 98, for maintaining a constant differential pressure across an orifice located downstream of the principal flow controller apparatus. Ambient air at a constant volumetric flow rate then exits the air pump subassembly through outlet 68 into a flow line 84. Flow line 84 communicates with inlet 86 to the local control assembly. In the configuration of FIG. 4, the ambient air introduced at inlet 86 passes through conventional solenoid value 116 and is vented to the air. When the concentration of combustible gases introduced through flow line 108 to sensor 112 exceeds the predetermined upper limit, solenoid valve 116 is actuated to introduce dilution air at a constant volumetric flow rate into flow line 118.

FIG. 5 shows the position of solenoid valve 116 for introducing dilution air into flow line 118. Flow line 118 communicates with sample flow line 108 upstream of sensor solenoid valve 110. Dilution air is mixed with the initial gas-air mixture to dilute the gas to a concentration which can be detected by sensor 112. When dilution air is introduced into flow line 108, the volumetric flow rate of the diluted gas-air mixture is greater than the volumetric flow rate of the initial gas-air mixture. The flow rate of the diluted gas-air mixture is, however, constant since the initial gas-air volumetric flow rate is constant and the volumetric flow rate of the dilution air introduced into flow line 108 is also constant. Sensor 112 must be capable of adequately detecting the gas concentration at both the initial volumetric flow rate and at the volumetric flow rate of the diluted gas-air mixture.

Figure 6:
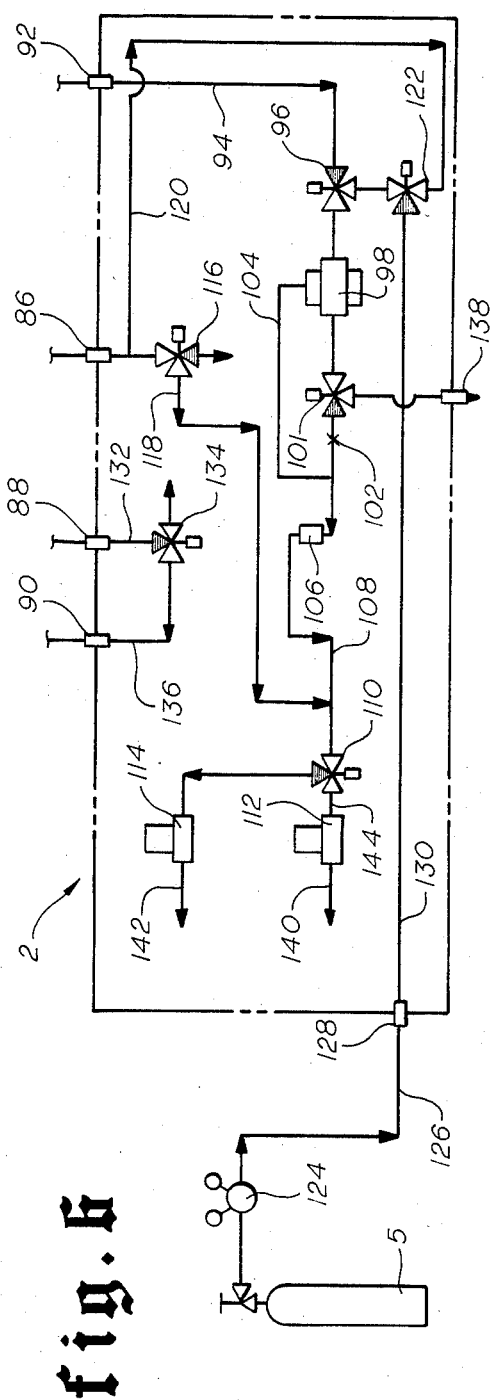
FIG. 6 is a flow schematic of the flow control subassembly showing the zero calibration flow regime.

The gas detection system comprising the preferred embodiment of this invention comprises means for automatically calibrating the sensors to ensure that variations of sensor sensitivity over time, or variations in ambient temperature or relative humidity are not incorrectly interpreted as an indication of a change in the concentration of gases entrained in the circulating drilling fluid. FIG. 6 depicts the condition of the local flow control subassembly 2 for delivering ambient air only to the sensor 112 for calibrating the sensor response to a sample containing no detectable gases. The flow of dilution air through flow line 118 is uninterrupted in the flow schematic of FIG. 6. However, the flow of sample air into the local control subassembly at inlet 92 is interrupted by solenoid valve 96. Valve 96 has been shifted its position shown in FIG. 5 to block the flow of the gas-air mixture sample. Solenoid valve 101 has also been actuated to vent any air-gas sample in flow controller 98 through vent 138. In this configuration, only dilution air in flow line 118 is exposed to the sensor 112, and an accurate zero reading for sensor 112 should be obtained. In the preferred embodiment of this invention, the zero calibration would be conducted periodically. Appropriate software in the controlling microprocessor would shift the appropriate solenoid valves for calibration.

An alternate flow path could also be used for conducting the zero calibration. Closing solenoid valve 116 to prevent the flow of dilution air in flow line 118 and opening solenoid valve 101 would still expose sensor 112 to ambient air containing no detectable gases, if solenoid valve 96 is retained in the closed position of FIG. 6. Dilution air in flow line 120 would enter through solenoid valve 122 and solenoid valve 96 and would pass through flow controller 98. Flow controller 98 would regulate the volumetric flow rate of ambient air and establish that rate at a value equal to the normal volumetric flow rate of the gas-air mixture sample. Of course there would be an initial flow of gas-air mixture in flow line 108, but after the initial gas-air mixture is flushed from flow line 108, only ambient air at a volumetric flow rate equal to the normal gas-air mixture flow rate would be exposed to sensor 112. Although the response of sensor 112 is dependent upon the flow rate of gas or air to which it is exposed, the absence of a detectable gas in either the dilution air or the ambient air passing through flow controller 98 should give the same zero reading.

Figure 7:
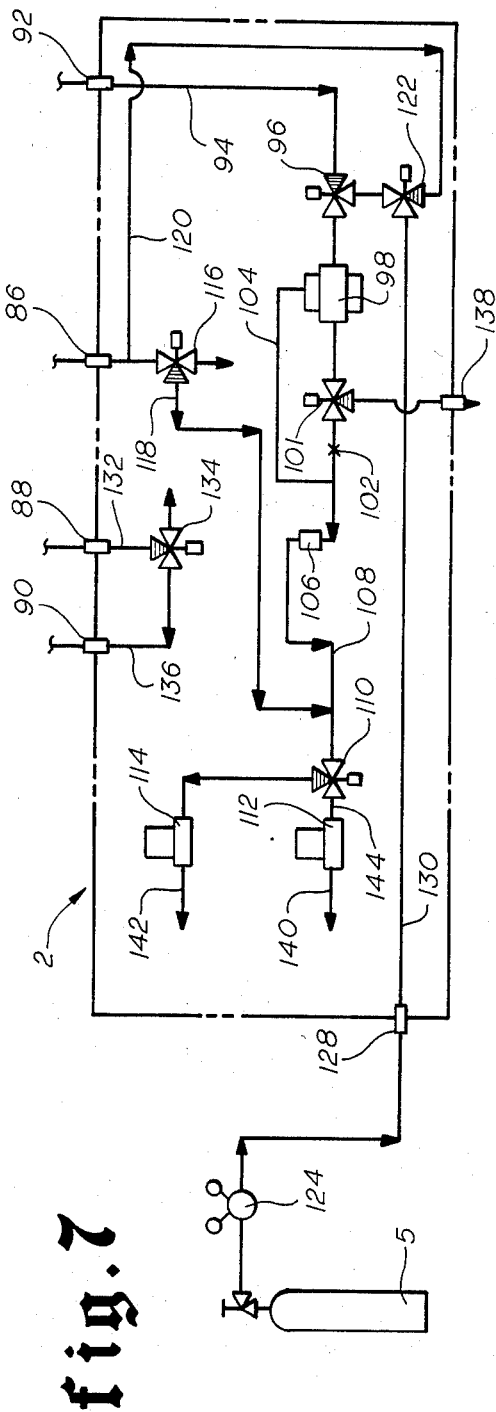
FIG. 7 is a flow schematic showing the span calibration flow regime to determine the response of sensors to a calibration gas.

In addition to calibrating the zero reading for sensor 112, it is also necessary to periodically calibrate the span response of sensor 112 to a detectable gas having a known concentration. FIG. 7 shows the configuration of the gas detection system for this span calibration. The normal flow of gas-air sample has been interrupted by closing solenoid valve 96. In the configuration of FIG. 7, the flow of dilution air into flow line 108 is interrupted by closing solenoid valve 116 and by closing flow line 120 by shifting solenoid valve 122. A calibration gas contained in a reservoir 5 is introduced into the local controller assembly through vent 128. In the preferred embodiment of this invention, the detectable gas contained in reservoir 5 comprises methane having a concentration of 2.5%. A conventional pressure regulator 124 maintains the pressure of the calibration gas introduced at inlet 128 at a value compatible with the gas detector. Valve 122 closing flow line 120 and opening flow line 130 introduces calibration gas through solenoid valve 96 into the sample flow controller 98. In this configuration, calibration gas is introduced to sensor 112 at the same volumetric flow rate as for the conventional gas-air mixture sample. Thus the response of sensor 112 to a detectable gas having a known concentration can be used to calibrate the system and to provide an accurate reading of the concentration of detectable gases in the gas-air mixture sample. The response of sensor 112 can be further calibrated by opening solenoid valve 116 to introduce dilution air at a known and constant volumetric flow rate to flow line 108 to intermix with the calibration gas. Since the volumetric flow rates of both the dilution air and the calibration gas are constant, the concentration of calibration gas will also be constant at the dilution flow rate. The response of the sensor 112 can thus be determined at the dilution flow rate.

In the preferred embodiment of this invention, the zero and span calibrations are conducted at regular intervals. Since valve 96 is closed during both the zero and span calibrations, no measurement can be made of the gas concentration in the gas-air mixture sample during the calibration sequence. However, the concentration of gases produced from the subterranean formation could be at a significant level at the time for conducting a regular calibration. This increased gas concentration, or gas show, could indicate an incipient gas kick and it may be desirable to constantly monitor the increasing levels of gas present in the gas-air mixture. Therefore the software in the microprocessor controlling the operation of the gas detection system can be programmed to prevent any calibration sequence if the level of gas detected by the sensors is above a predetermined level. Calibration would only occur after the gas levels have been reduced or upon a manual command from the driller.

Figure 8:
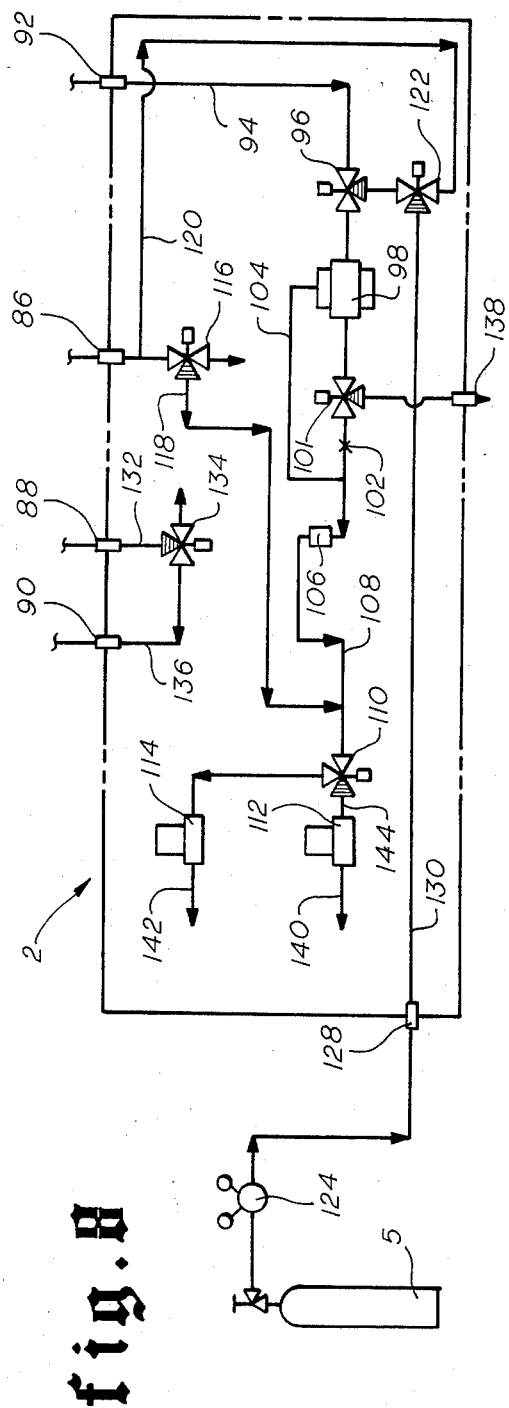
FIG. 8 is a flow schematic of the flow control subassembly showing the flow schematic in which an alternate sensor is employed.

In the preferred embodiment, two identical sensors 112 and 114 are provided. Sensor 114 is included as a backup for sensor 112. Solenoid valve 110 is provided to direct flow to either sensor 112 or sensor 114. In the configuration of FIGS. 5-7 only sensor 112 is exposed to a gas-air mixture sample. In the configuration of FIG. 8, the position of solenoid valve 110 has been shifted upon command from the microprocessor unit or as the result of a manual command and the gas-air mixture sample is exposed to identical sensor 114. The microporcessor controlling unit can determine if changes in the sensor reference voltage or signal corresponding to a zero gas concentration in excess of a presecribed drift have occurred. The microprocessor can also detect if the sensor voltage or signal continuously equals a prescribed maximum value in excess of a prescribed time. If the reference signal drift is excessive, the microprocessor will institute a calibration procedure by introducing calibration gas to the sensor. If the sensor output is equal to a maximum value for an excessive time, dilution air can be introduced to the sensor and any change in sensor output can be detected. If the sensor output does not change, a complete calibration can be instituted. An unsatisfactory sensor response to calibration will automatically switch the flow of the gas-air sample to the other sensor. Suitable control means can also be added to determine if the sensor has been contaminated.

The preferred embodiment of the gas detection system disclosed herein uses a commerically available combustible gas detection sensor to detect the presence of combustible gases contained in circulating drilling fluids. In the preferred embodiment of this invention, a combustible gas sensor, the Model 550 manufactured by Delphian Corporation is used. A description of the type sensor used herein is contained in U.S. Pat. No. 4,305,724. This sensor is a catalytic bead sensor of the hot wire type and uses an electrically conductive platinum wire. When a mixture of a combustible gas or vapor in air moves into the vicinity of the electrically conductive platinum wire, the combustible gas is oxidized. The sensor employed in the preferred embodiment of this invention uses a platinum wire enclosed in a ceramic bead which is coated with a highly active palladium or platinum catalyst. This oxidization reaction is exothermic which would cause an increase in the temperature of the bead and a resulting increase in the electrical resistance of the small platinum coil embedded in the ceramic bead. The change in resistance of the embedded platinum coil is proportional to the amount of chemical energy released by the oxidization reaction. A Wheatstone principle of constant voltage or current is employed and the electrical power to the bead is reduced as the temperature increases, with the electrical resistance of the embedded platnium coil being maintained essentially constant. The reduction of electrical power is linearly proportional to the combustible gas concentration. By preventing significant temperature increases, deteriorating sensitivity and burn out which would be expected to occur over time is reduced.

This conventional sensor element is a diffusion type sensor. A central flame arrestor or metal filter, such as a stainless steel gauze or wire mesh, encloses the catalytic bead sensor element. An equilibrium is established between the inwardly diffusing gas-air mixture and the outward diffusion of combustion byproducts. The sensor employed in the preferred embodiment of this invention comprises a diffusion type sensor for continuous monitoring of combustible hydrocarbons. Although sensors of this type have been used in gas well applications, these diffusion type sensors are primarily intended for monitoring rather than quantifying the level of ambient combustible hydrocarbons.

Figure 9:
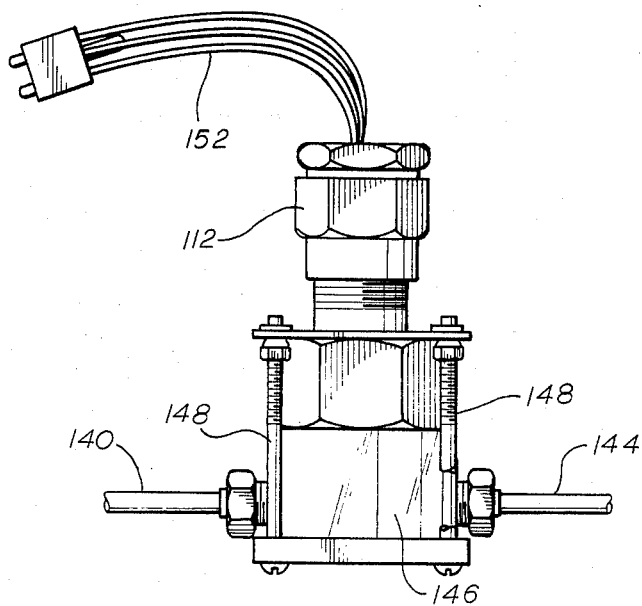
FIG. 9 is a view of an individual sensor.
Figure 10:
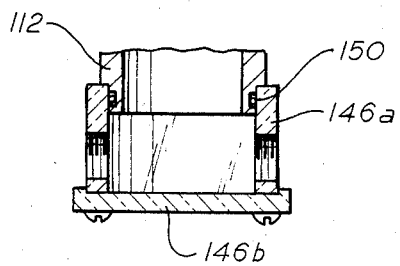
FIG. 10 shows the sensor mounting.

In the preferred embodiment of this invention, each sensor 112 or 114 is mounted to detect the presence of combustible hydrocarbons in a moving flow stream entering through path 108 and exiting through vents 140 or 142. FIG. 9 depicts a sensor mounting assembly having an inlet line 144 which communicates through solenoid valve 110 with flow line 108, and an outlet 140 which communicates with a vent positioned to dispose of any combustible gases without any significant explosion hazards. Venting of the combustible gas-air mixture in this manner is required by applicable safety regulations. The gas-air mixture exposed to sensors 112 and 114 is therefore transported past the sensors in a continuously moving flow stream.

FIG. 9 shows the sensor 112 mounted in a vertical position on a mounting bracket and attached to a flow chamber 146. Signal conductors 152 extend from the flow sensor and are interconnected with the microprocessor used to relay signals to appropriate output displays, to process signals received from the sensor. The ceramic coated platinum wire and the wire mesh diffusion filter (not shown) incorporated in the conventional sensor depicted herein are located within sensor element 112 above the flow chamber 146. Flow chamber 146 is secured to the sensor 112 by a plurality of bolts 148 attached to the base of the flow chamber 146. Flow chamber 146 comprises a right circular cylinder open at the upper end and comprising an integral base 146b at the lower end of the cylindrical walls 146a. An aligned inlet and outlet are located in opposed positions on the cylindrical wall 146a. The inlets and outlets provide for communication between the flow line 144 and the interior chamber and for venting through vent 140. The inlets and outlet are each spaced from the upper surface of the base 146b and the cross-sectional area defined between cylindrical walls 146a of the flow chamber is greater than the cross-sectional area of the inlet or outlet. Therefore flow entering flow chamber 146 is decelerated initially and is accelerated as it leaves through vent 140. Turbulence is, however, minimized by the alignment of the inlet and outlet and by the spacing of the inlets and outlet from the flow chamber base. In the preferred embodiment of this invention, the inlet line 144 and the outlet line 140 are oriented in a horizontal configuration with the sensor 112 being oriented vertically. Thus the gas-air sample mixture flows horizontally between inlet and outlet, and combustible gases reach the sensor element by vertical diffusion. The sensor element 112 is received within the upper end of cylindrical flow chamber walls 146a and an O-ring seal 150 prevents diffusion of gases on the exterior of sensor 112. All vertically diffusing gases reaching the ceramic bead sensor element must pass through the equilibrium metallic mesh diffusion filter which maintains an equilibrium between inwardly diffusing gases and outwardly diffusing combustion byproducts.

Figure 12:
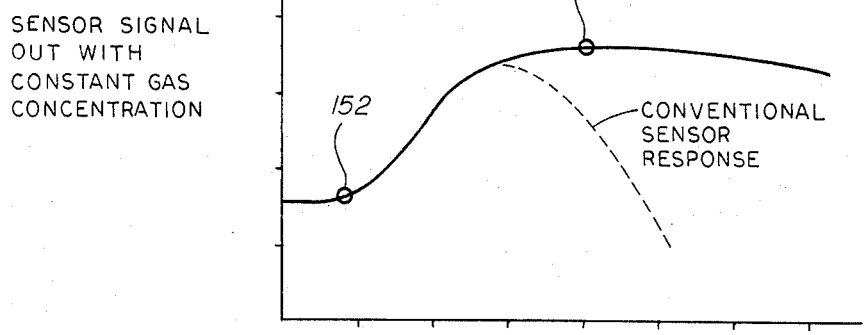
FIG. 12 shows the signal response for the sensor subassembly.

Conventional sensors of the type used herein display a sensor signal sensitivity to varying flow rate for a constant gas concentration. For conventional sensors, the sensor signal remains substantially constant for low flow rates but begins to increase dramatically at intermediate flow rates. The sensor signal, however, reaches a maximum and begins to substantially decrease at even larger volumetric flow rates unless the incoming flow is permitted to diffuse and is substantially stationary in the vicinity of the sensor. The gas detection system depicted herein must, however, maintain a continuous flow stream past the sensor in order to deliver a gas-air mixture at a sufficient rate to obtain a relatively quick response to changing gas concentrations and in order to vent the gas-air mixture to a safe location. In order to reduce the velocity of the incoming gas-air mixture to a flow rate at which the sensor signal is constant with the flow rate, an impractically large flow chamber or plenum chamber in the vicinity of the sensor would be necessary. It has been found, however, that mounting a conventional sensor in the flow chamber 146, a signal sensor response as shown in FIG. 12 can be obtained. For a constant gas concentration, the sensor signal will remain essentially constant at low levels of flow rate, but will increase in a conventional fashion at intermediate flow rate levels. At high flow rate levels, however, the sensor signal will become essentially constant, but a higher level than the initial sensor signal for low flow rates. In the gas detector comprising the preferred embodiment of this invention, the initial flow rate of the gas-air mixture sample entering through controller 98 and flow line 108 is essentially equal to the value represented in 152 and is within the range of flow rates at which the sensor signal remains essentially constant. When dilution air is added through flow line 118, the increased flow rate of the dilution air plus the gas-air mixture sample entering through controller 98 falls in the vicinity of point 154 at flow rates where the sensor signal is essentially constant and at a higher level than at point 152. Since the normal flow rates in the two flow regimes of interest lie in the separate constant regions, slight variations in flow rate from the optimum value which can occur within the obtainable volumetric flow rate accuracies of conventionally available flow controllers will not result in substantially different sensor signals and in false indications in changes in the gas concentration.

Figure 13:
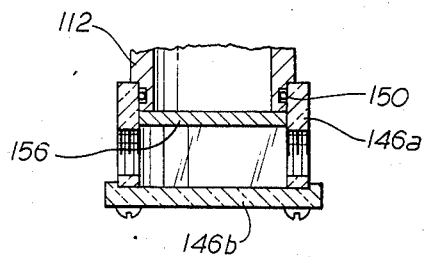
FIG. 13 is a view of an alternate embodiment of an individual sensor.
Figure 11:
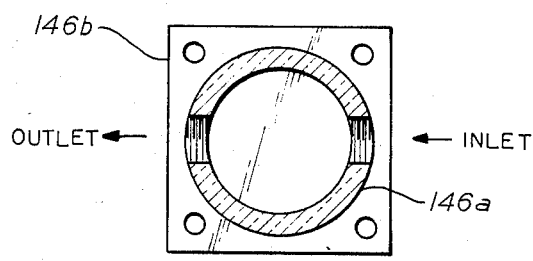
FIG. 11 is a plan view of the sensor mounting bracket.

FIG. 13 shows an additional modification for improving the capabilities of a conventional sensor of the type employed herein. A wire mesh filter screen 156 having an essentially constant porosity can be positioned at the lower end of sensor 112 between the inlet and outlet of flow chamber 146 and sensor 112. This additional filter screen can reduce the concentrations of gas in the gas-air mixture flow stream which are exposed to the sensor. Since the porosity of the additional filter screen 156 can be controlled, the sensor signal responding to the reduced gas concentrations above the flow stream can be processed by appropriate software in the accompanying microprocessor to reflect true values of the gas concentration in the flow stream below screen 156.

Although the invention has been described in terms of the specified embodiment which is set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. An apparatus for detecting the presence of a gas entrained in an aqueous fluid circulated through a subterranean well bore, comprising:
   a gas gathering means for gathering gas liberated from the circulating fluid for delivery to a sample gas flow line;
   a sample flow controller in said flow line comprising means for establishing a constant rate of sample gas flow; means for regulating the relative humidity of the constant rate sample gas flow to a fixed value less than 100%;
   sensor means for detecting the presence of gas in a gas sample flow;
   means for directing the fixed relative humidity, constant rate sample gas flow to the sensor means;
   a dilution flow line communicating with the gas flow line between the sample flow controller and the sensor means for reducing the concentration of the gas supplied to the sensor means and including valve means selectively communicating said dilution flow line with the gas flow line; and
   control means in communication with said sensor means and said valve means for establishing communication between the sample gas flow line and the dilution flow line when the concentration of gas in the circulating fluid exceeds a predetermined concentration, whereby the concentration of gas thereafter exposed to the sensor means is less than the predetermined concentration.

2. The apparatus of claim 1 further comprising output means in communication with the sensor means so as to generate a signal from the sensor means corresponding to the gas concentration in the sample gas flow line at concentrations above and below the predetermined concentration.

3. An apparatus for use for continuously detecting the concentration of gas as a subterranean well is drilled by monitoring the production of gas from a subterranean formation, comprising:
   gas trap means for gathering produced gases entrained in a water containing fluid circulated through the subterranean well bore to the well surface and mixing the produced gases with air to produce an air-gas mixture with a high water vapor content;
   a sample flow line extending from the gas trap means to a location spaced from the gas trap means;

pump means for pressurizing the air-gas-water vapor sample mixture to a level above ambient, thereby raising the relative humidity to about 100%;

means for removing excess water droplets;

means for reducing the pressure of the air-gas-water vapor sample mixture to a pressure level approaching ambient, thereby reducing the relative humidity of the gas-air-water vapor mixture to a constant level below 100%;

a flow controller in communication with the pressure reducing means comprising means for transporting the air-gas-water mixture at a constant flow rate;

a sensor comprising means for generating a signal in response to varying amounts of combustible gas;

a flow line transporting the air-gas-water vapor mixture from the flow controller to the sensor to expose the mixture to the sensor; and an output communicating with the sensor to continuously display the relative amount of combustible gas transported to the well surface.

4. An apparatus for use on a drilling rig for continuously detecting incipient gas kicks as a subterranean well is drilled by monitoring the production of gas from a subterranean formation; comprising:

gas trap means for gathering produced gases entrained in a water containing fluid circulated through the subterranean well bore to the well surface at the rig site in a location where combustible gases are present and mixing the produced gases with air to produce an air-gas mixture with a high water vapor content;

a sample flow line extending from the gas trap means to a location on the drilling rig spaced from the gas trap means;

pump means connected to said sample flow line for pressurizing the air-gas-water vapor sample mixture to a level above ambient, thereby raising the relative humidity to about 100%;

means for removing excess water droplets;

means for reducing the pressure of the gas-air-water vapor sample mixture to a pressure level approaching ambient, thereby reducing the relative humidity of the gas-air-water vapor mixture to a constant level below 100%;

a flow controller in communication with said pressure reducing means comprising means for transporting the air-gas-water vapor sample mixture at a constant flow rate;

a sensor comprising means for generating a signal in response to varying amounts of combustible gas;

a flow line transporting the air-gas-water vapor sample mixture from the flow controller to the sensor to expose the mixture to the sensor; and an output located at the drilling rig in a location spaced from combustible gases and in communication with the sensor to continuously display the relative amount of combustible gas transported to the well surface.

5. The apparatus of claim 4 further comprising means for automatically calibrating the response of the sensor to combustible gases.

6. In an apparatus for detecting incipient gas kicks in a subterranean well by detecting the presence of gases produced from a subterranean formation and entrained in a fluid circulated through a subterranean well, including a gas trap for gathering produced gases liberated from the circulating fluid;

a pump assembly transporting a liberated gas sample through a sample flow line;

a sensor for detecting the presence of produced gas in a gas sample and producing a signal output;

a flow controller connected between said pump assembly and said sensor for maintaining a constant flow rate of the gas sample to the sensor; and further comprising:

a calibration gas source containing gas of a known concentration;

a valve positioned and arranged so as to close the sample flow line upstream of the flow controller;

control means monitoring said signal output and selectively introducing calibration gas upstream of the flow controller, whereby calibration gas is exposed to the sensor to calibrate the response of the sensor to a known concentration of calibration gas transported at the constant rate established by the flow controller; and means for separately transporting gas-free ambient air through the flow controller to the sensor to calibrate the response of the sensor to a zero concentration of produced gas.

7. The apparatus of claim 6 wherein the control means further comprises means for continuously monitoring the signal output from the sensor corresponding to the absence of produced gases;

means for establishing a prescribed reference signal drift; and means for detecting a change in the signal output exceeding the reference signal drift, whereby the control means introduces calibration gas upstream of the flow controller when the signal output change exceeds the prescribed reference signal drift.

8. The apparatus of claim 7 further comprising a second sensor and means for introducing the gas sample to the second sensor when the reference signal change of the first mentioned sensor exceeds the prescribed reference signal drift.

9. The apparatus of claim 6 wherein the control means further comprises means establishing a maximum sensor drift; means for monitoring the elapsed time for which the sensor output is continuously equal to the maximum sensor output; and means for introducing additional air to the sensor when the elapsed time for which the sensor output is continuously equal to the maximum sensor output exceeds a prescribed value, whereby any change in the sensor output in response to introduction of additional air is detected.

10. The apparatus of claim 9 wherein the control means includes means for introducing calibration gas upstream of the flow controller in the absence of a change in the sensor output in response to introduction of the additional air.

11. The apparatus of claim 6 wherein the means for transporting gas free ambient air through the flow controller comprises a flow line communicating with the valve upstream of the flow controller and a second valve.

12. The apparatus of claim 11 wherein the means for introducing calibration gas upstream of the flow controller comprises a flow line between the calibration gas source and the second valve, calibration gas being transported to the flow controller when the second valve is in one position and gas free ambient air being transported to the flow controller when the second valve is in another position open to ambient air.

13. The apparatus of claim 6 further comprising means for introducing ambient air at a flow rate in excess of the constant flow rate of sample gas between the flow controller and the sensor to dilute the concentration of calibration gas, whereby the degree of dilution can be calibrated and the response of the sensor to dilution of sample gas can be calibrated.

14. The apparatus of claim 6 further comprising means for monitoring the signal from the sensor in response to varying amounts of produced gases and means for preventing the introduction of calibration gas or ambient air through the flow controller when the signal exceeds a predetermined value.

15. The apparatus of claim 6 wherein the sensor comprises means for detecting the presence of combustible gases.

16. A method of detecting the presence of gas entrained in a fluid circulated through a subterranean well bore, comprising the steps of:
liberating the gas from the circulating fluid for delivery of a sample thereof to a sample gas flow line;
establising a constant rate of sample gas flow;
introducing the sample gas flow to a sensor for detecting the presence of gas in the sample flow line;
establishing a constant gas sample relative humidity of less than 100% at the sensor; and
introducing air to selectively dilute the gas sample when the gas concentration at the sensor exceeds a predetermined concentration;
establishing a second constant rate of flow of the diluted gas sample to the sensor whereby the maximum sensitivity of the sensor is not exceeded.

17. A method of detecting incipient gas kicks in a subterranean well bore due to the production of gas from a subterranean formation; comprising the steps of:
liberating produced gases entrained in a water containing fluid circulated through the subterranean well bore;
mixing the produced gases with air and transporting the gas-air-water vapor mixture to a flow line;
removing at least a portion of any solids or liquid droplets entrained in the gas-air-water vapor mixture; reducing the temperature of the remaining gas-air-water vapor mixture to condense water vapor in the gas-air-water vapor mixture;
increasing the pressure of the gas-air-water vapor mixture by a pump the remaining mixture being essentially saturated with water vapor at the increased pressure;
removing condensed water vapor from the pressurized remaining mixture downstream of the pump;
reducing the pressure of the remaining mixture to lower the relative humidity of the remaining gas-air-water vapor mixture to an essentially constant value less than 100%;
establishing a constant flow rate for the constant humidity remaining mixture in the flow line;
exposing the constant humidity remaining mixture to a sensor responsive to varying amounts of produced gases in the constant humidity remaining mixture to detect the relative amount of produced gases so that incipient kicks due to increasing production of gases from a subterranean formation can be detected.

18. The method of claim 17 comprising the further step of mixing additional air with the constant humidity gas-air-water vapor mixture after establishment of the constant flow rate of the constant humidity gas-air-water vapor mixture when the concentration of produced gas exposed to the sensor exceeds a predetermined value to dilute the concentration of produced gases in the constant humidity gas-air-water vapor mixture exposed to the sensor.

19. The method of claim 18 wherein the constant humidity gas-air-water vapor mixture is exposed to the sensor at only two essentially constant flow rates, the flow rate of the diluted constant humidity gas-air-water vapor mixture exceeding the initial flow rate of the undiluted constant humidity gas-air-water vapor mixture.

20. The method of claim 17 comprising the further step of venting a portion of the gas-air-water vapor mixture at a constant rate to increase the flow rate of the portion of the gas-air-water vapor mixture remaining in the flow line.

21. The method of claim 20 wherein the flow rate of gas-air-water mixture transported to the flow line is constant.

22. The method of claim 17 comprising the further step of intermittently exposing the sensor to a calibration gas of known concentration and alternatively to ambient air containing no produced gases to calibrate the sensor.

23. The method of claim 17 comprising the further step of simultaneously introducing calibrated gas and ambient air at the same volumetric flow rate at which additional air is added to dilute the gas-air-water mixture, to calibrate the degree of dilution and the response of the sensor to dilution.

* * * * *